(12) United States Patent
Fujita et al.

(10) Patent No.: US 11,541,142 B2
(45) Date of Patent: Jan. 3, 2023

(54) FRAGRANCE MATERIAL HOLDING MEMBER AND FRAGRANCE PROVIDING DEVICE

(71) Applicant: Sony Corporation, Tokyo (JP)

(72) Inventors: Shuji Fujita, Tokyo (JP); Yuji Ishigaki, Tokyo (JP); Yukari Tsunoda, Tokyo (JP); Koya Nomoto, Aichi (JP); Tsunetoshi Samukawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/768,572

(22) PCT Filed: Aug. 17, 2016

(86) PCT No.: PCT/JP2016/074048
§ 371 (c)(1),
(2) Date: Apr. 16, 2018

(87) PCT Pub. No.: WO2017/068842
PCT Pub. Date: Apr. 27, 2017

(65) Prior Publication Data
US 2018/0311397 A1    Nov. 1, 2018

(30) Foreign Application Priority Data

Oct. 23, 2015   (JP) .............................. JP2015-208661

(51) Int. Cl.
*A61L 9/12*      (2006.01)
*A61L 9/03*      (2006.01)
*A61L 9/14*      (2006.01)

(52) U.S. Cl.
CPC .............. *A61L 9/127* (2013.01); *A61L 9/037* (2013.01); *A61L 9/12* (2013.01); *A61L 9/14* (2013.01)

(58) Field of Classification Search
CPC . A61L 9/037; A61L 9/12; A61L 9/127; A61L 9/14
(Continued)

(56) References Cited

U.S. PATENT DOCUMENTS 2,562,959 A    8/1951   Stern
7,499,632 B2 *  3/2009  Granger .............. A01M 1/2033
                                              392/386
(Continued)

FOREIGN PATENT DOCUMENTS

DE   10 2009 015582 A1    10/2010
FR        3019047 A1 *    10/2015    ............... A61L 9/12
(Continued)

OTHER PUBLICATIONS

International Search Report and English translation thereof dated Nov. 22, 2016 in connection with International Application No. PCT/JP2016/074048.
(Continued)

*Primary Examiner* — Jason J Boeckmann
(74) *Attorney, Agent, or Firm* — Wolf, Greenfield & Sacks, P.C.

(57) ABSTRACT

[Object] To propose a novel and improved fragrance material holding member and fragrance providing device that can improve persistence of a fragrance material while avoiding an increase in the size of the device.
[Solution] Provided is a fragrance material holding member including: an airflow passage through which air supplied from an airflow source passes, the airflow passage being provided to penetrate the fragrance material holding member; and a holding space that branches from the airflow passage and holds a fragrance material.

11 Claims, 18 Drawing Sheets

(58) Field of Classification Search
USPC .................................................... 239/34–60
See application file for complete search history.

(56) References Cited

U.S. PATENT DOCUMENTS

| | | | |
|---|---|---|---|
| 8,833,366 B2* | 9/2014 | Colombo | A01M 1/2044 128/204.13 |
| 2008/0216850 A1 | 9/2008 | Li | |
| 2010/0288847 A1 | 11/2010 | Gruenbacher et al. | |
| 2015/0209465 A1* | 7/2015 | Slade | A61L 9/122 422/124 |
| 2016/0007649 A1 | 1/2016 | Sampson | |

FOREIGN PATENT DOCUMENTS

| | | |
|---|---|---|
| JP | 62-131802 U | 8/1987 |
| JP | 08-057030 A | 3/1996 |
| JP | H10210964 A | 8/1998 |
| JP | 2002-315975 A | 10/2002 |
| JP | 2010029168 A | 2/2010 |
| JP | 2010520754 A | 6/2010 |
| JP | 2014-067293 A | 4/2014 |
| JP | 2015-077404 A | 4/2015 |
| WO | WO1993008676 A2 * | 5/1993 |
| WO | WO 2010/132565 A1 | 11/2010 |

OTHER PUBLICATIONS

Written Opinion and English translation thereof dated Nov. 22, 2016 in connection with International Application No. PCT/JP2016/074048.

International Preliminary Report on Patentability and English translation thereof dated May 3, 2018 in connection with International Application No. PCT/JP2016/074048.

Extended European Search Report dated Jul. 18, 2018 in connection with European Application No. 16857160.2.

* cited by examiner

FRAGRANCE MATERIAL HOLDING MEMBER AND FRAGRANCE PROVIDING DEVICE

CROSS-REFERENCE TO RELATED APPLICATIONS

This is a U.S. National Stage Application under 35 U.S.C. § 371, based on International Application No. PCT/JP2016/074048, filed in the Japanese Patent Office as a Receiving Office on Aug. 17, 2016, entitled "PERFUME RETAINING MEMBER AND SCENT PROVIDING DEVICE", which claims priority under 35 U.S.C. § 119(a)-(d) or 35 U.S.C. § 365(b) to Japanese Patent Application Number JP2015-208661, filed in the Japanese Patent Office on Oct. 23, 2015, each of which applications is hereby incorporated by reference in its entirety.

TECHNICAL FIELD

The present disclosure relates to a fragrance material holding member and a fragrance providing device.

BACKGROUND ART

In recent years, technologies related to a fragrance providing device that provides a fragrance to the outside of the device have been proposed. For example, a technology of providing a fragrance by releasing a vaporized fragrance material by flow of air has been proposed (for example, see Patent Literature 1).

CITATION LIST

Patent Literature

Patent Literature 1: JP 2014-67293A

DISCLOSURE OF INVENTION

Technical Problem

Here, in the conventional technology, an increase in the amount of the fragrance material for improved persistence of the fragrance material may cause the need to increase the size of a member that accommodates the fragrance material. Thus, the device itself is increased in size in some cases. Therefore, in a fragrance providing device that provides a fragrance, it seems to be desirable to further improve persistence of a fragrance material while avoiding an increase in the size of the device.

Hence, the present disclosure proposes a novel and improved fragrance material holding member and fragrance providing device that can improve persistence of a fragrance material while avoiding an increase in the size of the device.

Solution to Problem

According to the present disclosure, there is provided a fragrance material holding member including: an airflow passage through which air supplied from an airflow source passes, the airflow passage being provided to penetrate the fragrance material holding member; and a holding space that branches from the airflow passage and holds a fragrance material.

In addition, according to the present disclosure, there is provided a fragrance providing device including: a fragrance material holding member including an airflow passage through which air supplied from an airflow source passes, the airflow passage being provided to penetrate the fragrance material holding member, and a holding space that branches from the airflow passage and holds a fragrance material; and the airflow source that supplies the air to the airflow passage.

Advantageous Effects of Invention

As described above, according to the present disclosure, persistence of a fragrance material can be improved while an increase in the size of the device is avoided.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
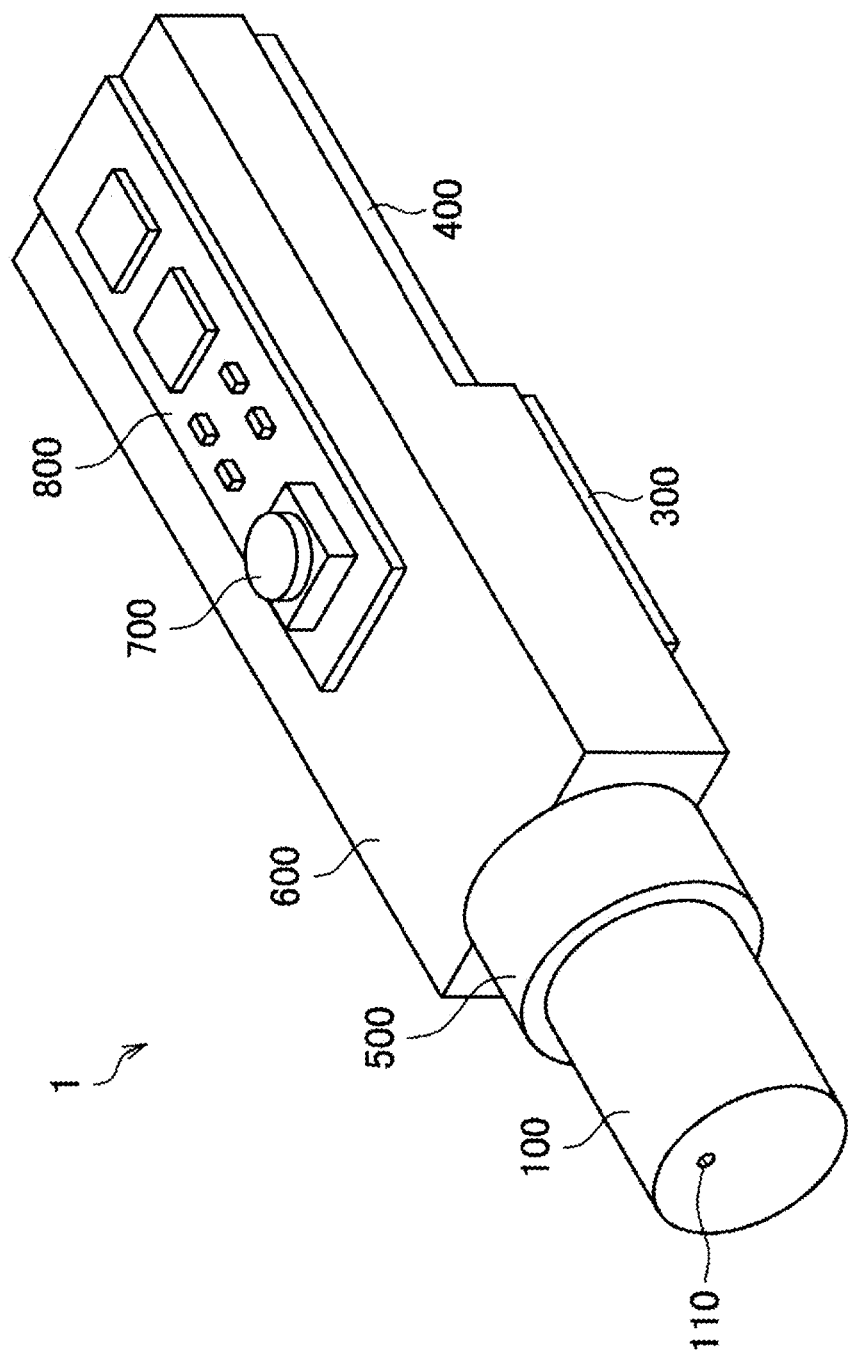
FIG. 1 is a perspective view of an example of a fragrance providing device according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be given in the following order.
1. Fragrance providing device
2. Fragrance material holding member
2-1. First example
2-2. Second example
2-3. Effect
3. Modification examples
3-1. First modification example
3-2. Second modification example
3-3. Third modification example
3-4. Fourth modification example
3-5. Fifth modification example
4. Conclusion

1. Fragrance Providing Device

Figure 2:
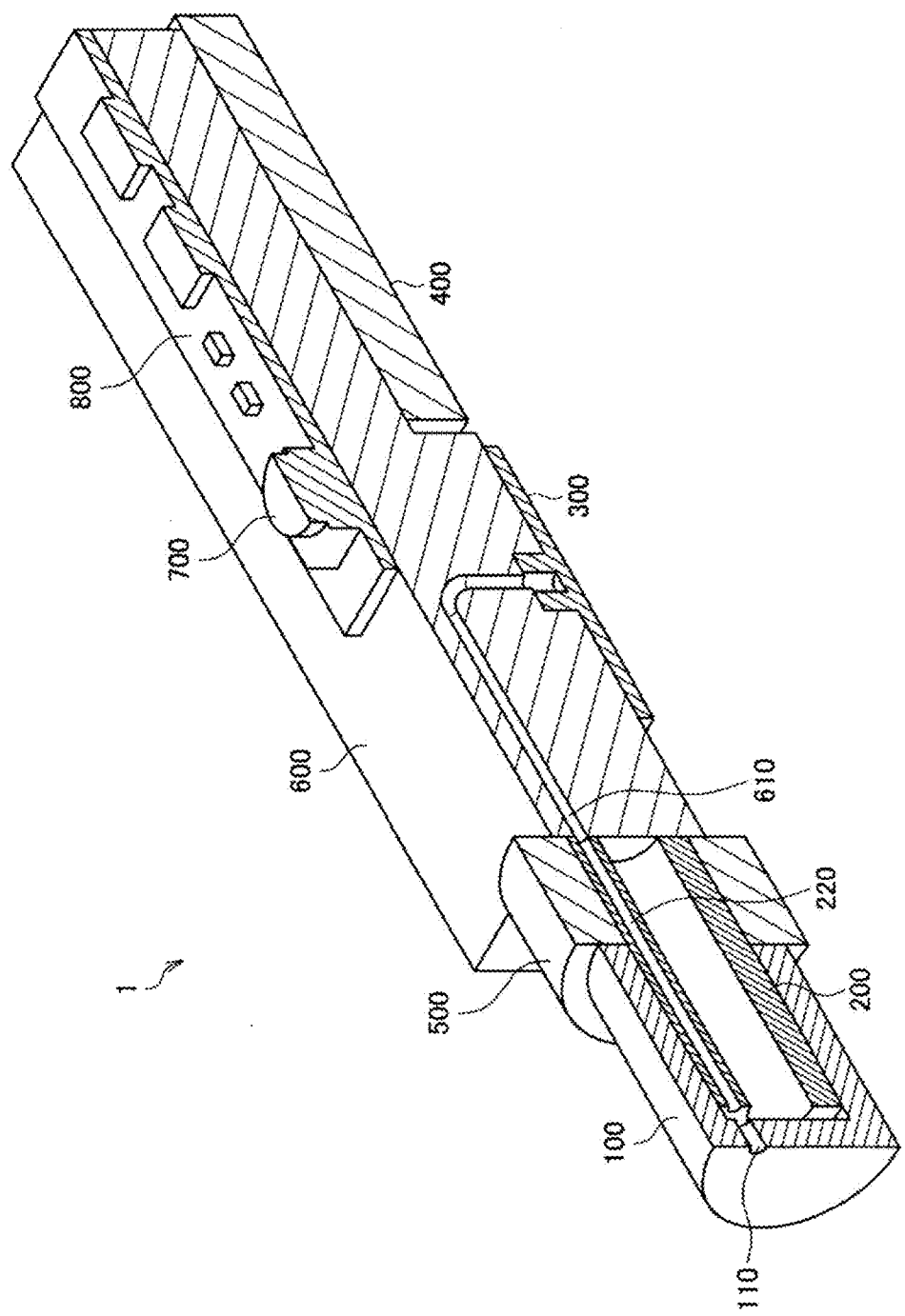
FIG. 2 is a cross-sectional perspective view of an example of the fragrance providing device according to the embodiment.
Figure 3:
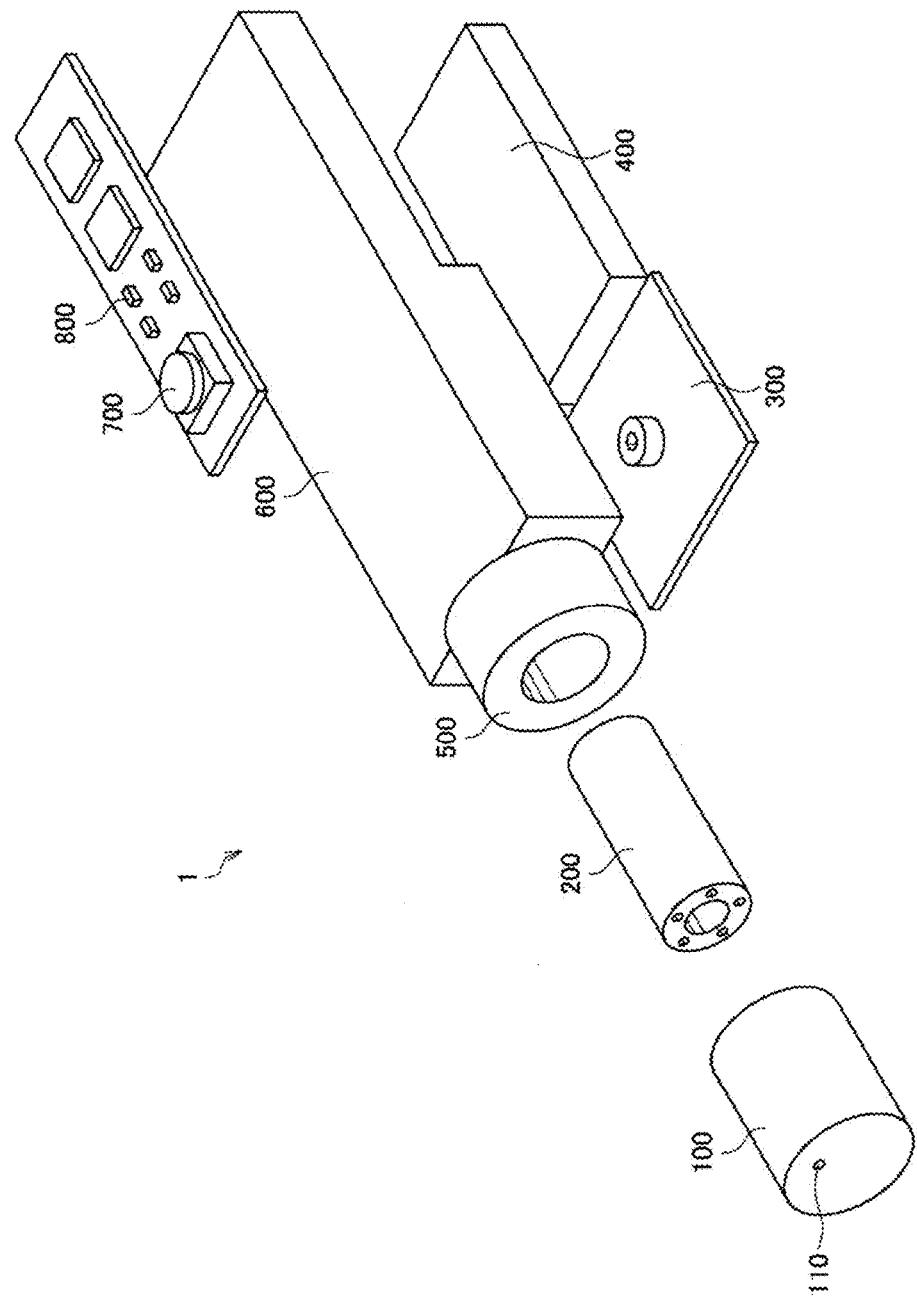
FIG. 3 is an exploded perspective view of an example of the fragrance providing device according to the embodiment.

First, a fragrance providing device 1 according to the present embodiment is described with reference to FIGS. 1 to 5. FIG. 1 is a perspective view of an example of the fragrance providing device 1 according to the present embodiment. FIG. 2 is a cross-sectional perspective view of an example of the fragrance providing device 1 according to the present embodiment. FIG. 3 is an exploded perspective view of an example of the fragrance providing device 1 according to the present embodiment. Note that in the following description, the side on which a discharge port 110 of a lid 100 is disposed in the fragrance providing device 1 is called a front end side.

As illustrated in FIGS. 1 to 3, the fragrance providing device 1 according to the present embodiment includes the lid 100, a fragrance material holding member 200, an air pump 300, a battery 400, a rotation mechanism 500, a chassis 600, a switch 700, and a substrate 800.

The lid 100 is a member that separates the fragrance material holding member 200 from the outside. The lid 100 has, for example, a tubular shape that is open on a rear end side, as illustrated in FIGS. 1 to 3. On the front end side of the lid 100 is provided the discharge port 110 from which air including a vaporized fragrance material sent from the fragrance material holding member 200 is discharged. The discharge port 110 is provided to communicate with a front end part of an airflow passage 220 through which air is supplied among a plurality of airflow passages 220 provided in the fragrance material holding member 200. An inner diameter of the discharge port 110 may be larger than an inner diameter of the airflow passage 220.

The fragrance material holding member 200 is a member that holds a fragrance material. The fragrance material holding member 200 has, for example, a hollow tubular shape as illustrated in FIGS. 2 and 3. As illustrated in FIG. 2, in the fragrance material holding member 200, the airflow passage 220 through which air supplied from the air pump 300, which is an example of an airflow source according to the present disclosure, passes is provided to penetrate the fragrance material holding member 200. In addition, the fragrance material holding member 200 is provided with a holding space that branches from the airflow passage 220 and holds the fragrance material. The fragrance material may be held by the airflow passage 220, in which case the fragrance material is held in a state of adhering to an inner surface of the airflow passage 220. Furthermore, in the holding space, the fragrance material may be held in a state of adhering to an inner surface of the holding space, or may be held in a state of filling the holding space. Specifically, the fragrance material may be an essential oil, an essential oil diluted in ethanol, or the like. One or a plurality of pairs of the airflow passage 220 and the holding space may be provided. Described below as an example is an example in which a plurality of pairs of the airflow passage 220 and the holding space are provided. In addition, an example in which the fragrance material is held by the airflow passage 220 is mainly described below.

The plurality of airflow passages 220 are provided at equal intervals on a circumference around a central axis of the fragrance material holding member 200, for example, and are provided in a straight-line from the rear end side to the front end side. The air supplied from the air pump 300 flows in from a rear end part of the airflow passage 220 via a flow channel 610 of the chassis 600, and is released from a front end part. This causes flow of air from the rear end side to the front end side of the airflow passage 220. A vaporized component of the fragrance material held by the airflow passage 220 is sent to the front end side of the airflow passage 220 by the flow of air caused in the airflow passage 220. In addition, a non-vaporized portion of the fragrance material held by the holding space does not flow out to the airflow passage 220 from the holding space, whereas the vaporized component of the fragrance material flows out to the airflow passage 220 via a branch part between the holding space and the airflow passage 220 and is sent to the front end side of the airflow passage 220 by the flow of air caused in the airflow passage 220. Then, the vaporized component of the fragrance material sent to the front end side of the airflow passage 220 is discharged from the discharge port 110 of the lid 100.

Examples of a constituent material of the airflow passage 220 and the holding space include a resin such as an acrylic resin, a urethane resin, an ABS resin, polyetheretherketone (PEEK), polyacetal (POM), a silicone resin, a fluorine resin, an olefin polymer resin, or a polyimide resin, a metal such as stainless steel, and glass. Specifically, a constituent material of the airflow passage 220 and the holding space may be selected in consideration of chemical resistance, weather resistance, strength, and the like. The inner diameter of each of the airflow passage 220 and the holding space may be set to a value smaller than 1 mm, as an example. Each of the airflow passage 220 and the holding space that is a micro flow channel having such a small inner diameter may be produced by laminate molding using a 3D printer, for example.

As the inner diameter of the airflow passage 220 is smaller, the occurrence of turbulent flow of a fluid in the airflow passage 220 is suppressed more easily and the flow of the fluid is more likely to be a laminar flow. In addition, in the case where the output of the air pump 300 is constant, as the inner diameter of the airflow passage 220 is smaller, air flows faster in the airflow passage 220. Thus, in the fragrance providing device 1 according to the present embodiment, straightness of air including the vaporized component of the fragrance material discharged from the discharge port 110 is improved. Therefore, by causing the air including the vaporized component of the fragrance material to be discharged toward a user of the fragrance providing device 1, the user can be provided with a fragrance without influence on the user's surroundings.

In addition, as the inner diameter of the airflow passage 220 is smaller, the proportion of an area in which the fragrance material is held with respect to an area in which air passes is larger in a transverse section in the airflow passage 220, and thus, the proportion of the fragrance material included in the air that is discharged from the discharge port 110 by the flow of air caused in the airflow passage 220 is larger. This enables a fragrance to be provided to the user more reliably. In addition, dimensions of the entire device can be reduced by making the inner diameter of the airflow passage 220 or the holding space smaller, which enables a reduction in the weight of the entire device. Therefore, the fragrance providing device 1 can be carried easily. Note that details of a configuration of the airflow passage 220 and the holding space of the fragrance material holding member 200 will be given later.

The air pump 300 is an example of an airflow source according to the present disclosure. For example, the air pump 300 supplies air to part of the plurality of airflow passages 220 of the fragrance material holding member 200 via the flow channel 610. The air pump 300 is, for example, electrically connected to the battery 400 via the substrate 800, and is driven by electric power supplied from the battery 400. Specifically, the air pump 300 includes a diaphragm to which a piezoelectric element is attached, and performs air blowing by deforming the diaphragm by application of an alternating current to the piezoelectric element. Note that the type of air blowing of the air pump 300 is not limited to this example, and for example, may be a fin type, a cylinder type, or the like. In addition, the air pump 300 may be of a manual type, in which case the battery 400, the switch 700, and the substrate 800 may be omitted from the configuration of the fragrance providing device 1.

The battery 400 stores electric power for operating the air pump 300. The battery 400 may be a primary battery capable of only discharging, or may be a secondary battery capable of charging as well.

The rotation mechanism 500 has a function of enabling switching of the airflow passage 220 through which air is supplied among the plurality of airflow passages 220 of the fragrance material holding member 200. Specifically, the rotation mechanism 500 is capable of relatively rotating the fragrance material holding member 200 and a member provided with a flow channel that communicates with part of the plurality of airflow passages 220 and introduces the air supplied from the air pump 300 to part of the airflow passages 220, in a manner that the airflow passage 220 that communicates with the flow channel is switched. More specifically, the rotation mechanism 500 is capable of relatively rotating the chassis 600 and the fragrance material holding member 200, in a manner that the airflow passage 220 that communicates with the flow channel 610 of the chassis 600 is switched. Note that FIG. 2 illustrates the flow channel 610 of the chassis 600 as an air flow channel between the air pump 300 and the airflow passage 220; however, another flow channel may be present between the flow channel 610 of the chassis 600 and the airflow passage 220. In that case, a member provided with the other flow channel and the fragrance material holding member 200 may be configured to be relatively rotatable by the rotation mechanism 500.

The chassis 600 is provided with the air pump 300, the battery 400, the rotation mechanism 500, and the substrate 800. In addition, the chassis 600 may be provided with wiring that electrically connects components, as necessary.

The switch 700 is provided on the substrate 800 to switch a drive state of the air pump 300. The substrate 800 is electrically connected to the battery 400, and for example, when the switch 700 is pressed by the user, electric conduction to a drive circuit for driving the air pump 300 that is installed on the substrate 800 is performed. Thus, the drive state of the air pump 300 is switched in accordance with the state of pressing of the switch 700 by the user.

Figure 4:
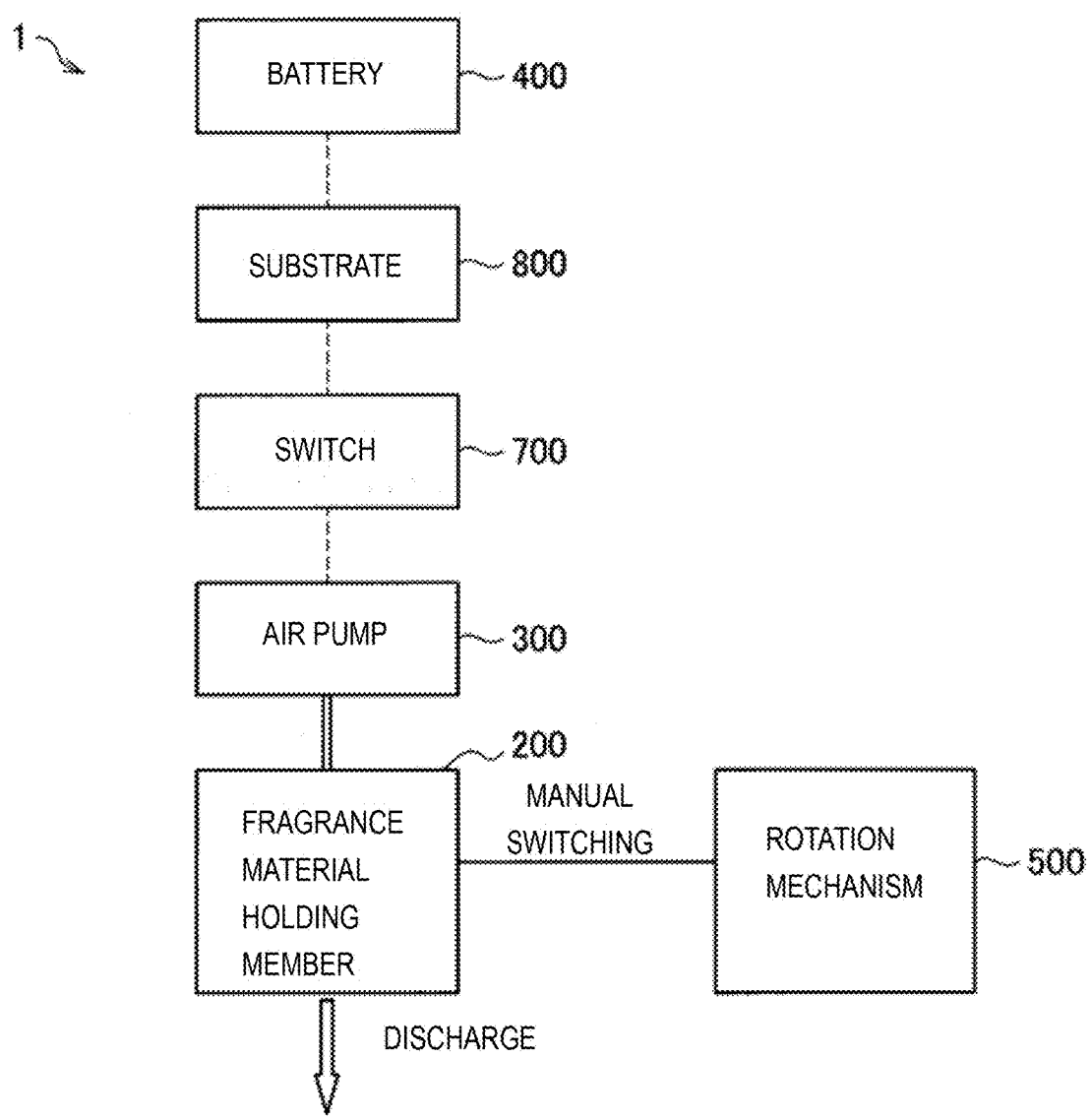
FIG. 4 is a system block diagram illustrating an example of the fragrance providing device according to the embodiment.

FIG. 4 is a system block diagram illustrating an example of the fragrance providing device 1 according to the present embodiment. As illustrated in FIG. 4, the battery 400 and the substrate 800 are electrically connected to each other. Then, when the switch 700 is pressed, electric conduction to the drive circuit for driving the air pump 300 that is installed on the substrate 800 is performed, and the air pump 300 is driven. Thus, the air pump 300 starts air blowing, and the air supplied from the air pump 300 is sent to the airflow passage 220 of the fragrance material holding member 200. Then, the vaporized component of the fragrance material held by the airflow passage 220 and the holding space of the fragrance material holding member 200 is discharged to the outside from the discharge port 110 of the lid 100. Switching of the airflow passage 220 to which air is introduced among the plurality of airflow passages 220 of the fragrance material holding member 200 by the rotation mechanism 500 is performed manually.

Figure 5:
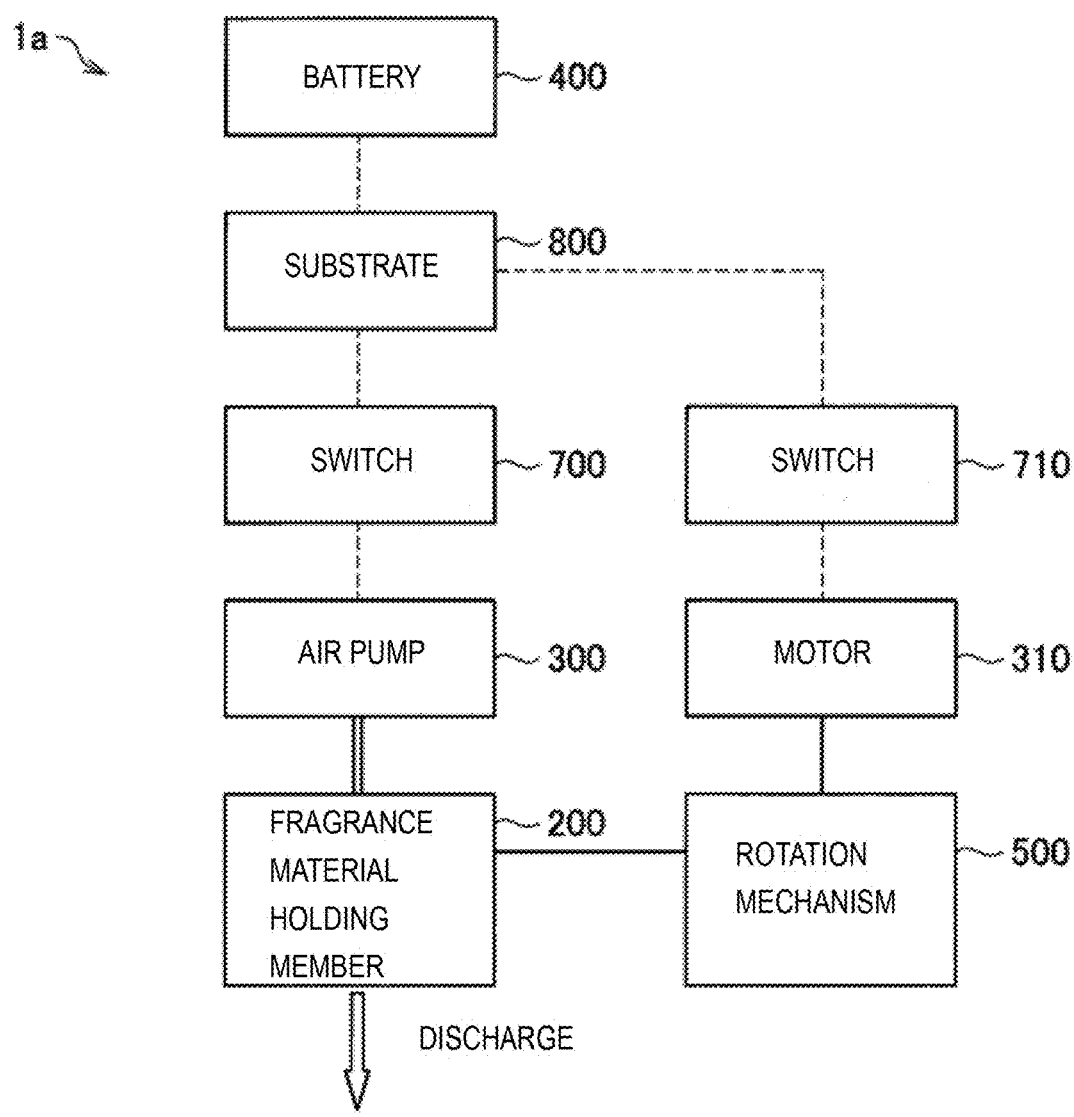
FIG. 5 is a system block diagram illustrating an example of a fragrance providing device according to another embodiment.

In this specification, the fragrance providing device 1 in which switching of the airflow passage 220 to which air is introduced by the rotation mechanism 500 is performed manually is mainly described, as described using FIG. 4; however, the type of switching by the rotation mechanism 500 is not limited to this example, and for example, the rotation mechanism 500 may be driven by a motor. Such a fragrance providing device 1a according to another embodiment includes a motor 310 that drives the rotation mechanism 500, and a switch 710 that switches electric conduction to a drive circuit for driving the motor 310 that is installed on the substrate 800. According to the fragrance providing device 1a, for example, as illustrated in FIG. 5, when the switch 710 is pressed, electric conduction to the drive circuit for driving the motor 310 that is installed on the substrate 800 is performed, and the motor 310 is driven. Thus, the rotation mechanism 500 is driven by the motor 310, and switching of the airflow passage 220 to which air is introduced among the plurality of airflow passages 220 of the fragrance material holding member 200 by the rotation mechanism 500 is performed.

2. Fragrance Material Holding Member

2-1. First Example

Figure 6:
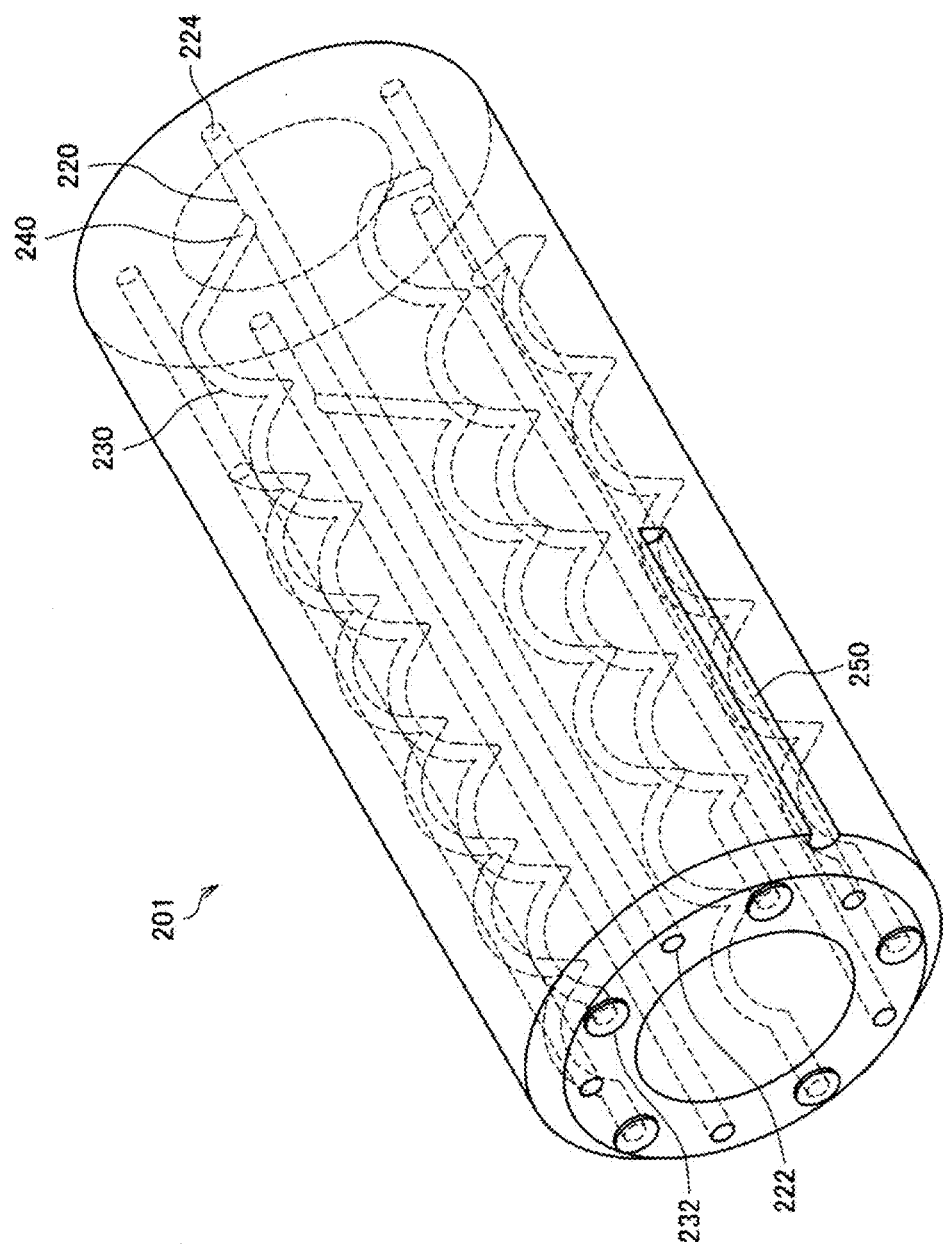
FIG. 6 is a perspective view of an example of a configuration of a fragrance material holding member according to a first example.
Figure 7:
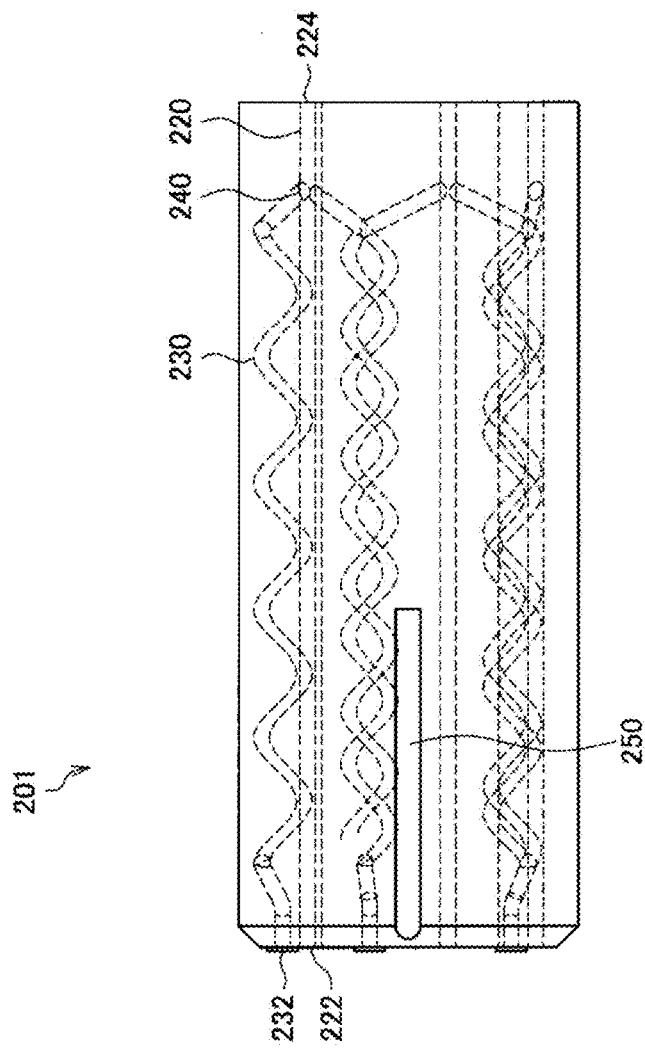
FIG. 7 shows a plan view and a side view of an example of a configuration of the fragrance material holding member according to the first example.
Figure 7:
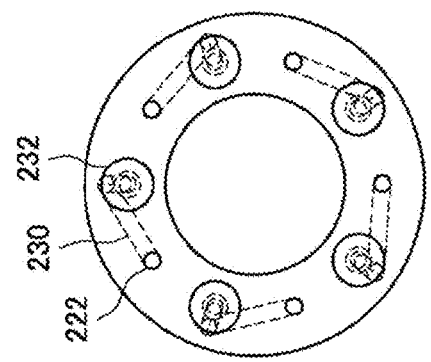

Now, a fragrance material holding member 201 according to a first example will be described with reference to FIGS. 6 to 8. FIG. 6 is a perspective view of an example of a configuration of the fragrance material holding member 201 according to the first example. FIG. 7 shows a plan view and a side view of an example of a configuration of the fragrance material holding member 201 according to the first example. As illustrated in FIGS. 6 and 7, the fragrance material holding member 201 includes the airflow passage 220, a holding space 230, and a locking groove 250.

The airflow passage 220 is provided to penetrate the fragrance material holding member 201, and the air supplied from the air pump 300 passes through the airflow passage 220. The air supplied from the air pump 300 flows in from an inlet 222, which is one end of the airflow passage 220, and is released from an outlet 224, which is the other end of the airflow passage 220. In addition, a fragrance material may be held by the airflow passage 220. For example, as illustrated in FIGS. 6 and 7, a plurality of airflow passages 220 are provided in a straight-line form in the axial direction of the fragrance material holding member 200, and the inlet 222 and the outlet 224 are formed respectively on a rear end face and a front end face of the fragrance material holding member 200. Furthermore, the airflow passage 220 may be provided on a circumference around the central axis of the fragrance material holding member 200. In that case, the rotation mechanism 500 is configured to be able to rotate the fragrance material holding member 200 with respect to the chassis 600 around the central axis of the fragrance material holding member 200. Thus, the airflow passage 220 that communicates with the flow channel 610 of the chassis 600 located on the rear end side of the fragrance material holding member 200 can be switched by rotating the fragrance material holding member 200.

Note that a path of the airflow passage 220 does not need to be in a straight-line form, and may have a curve shape, for example. In addition, the inlet 222 or the outlet 224 may be formed on an outer circumferential surface of the fragrance material holding member 200. In that case, the position of the flow channel 610 of the chassis 600 or the position of the discharge port 110 of the lid 100 is set at a position communicatable respectively with the inlet 222 or the outlet 224.

The holding space 230 branches from the airflow passage 220 and holds a fragrance material. For example, the holding space 230 is provided for each of the plurality of airflow passages 220, as illustrated in FIGS. 6 and 7. In the case where a fragrance material is held by the airflow passage 220, the holding space 230 holds a fragrance material the same in type as the fragrance material held by the airflow passage 220 that communicates with the holding space 230. Note that two or more holding spaces 230 may be provided for one airflow passage 220. The holding space 230 branches from a branch part 240 located on the outlet 224 side of the airflow passage 220, and is provided to extend from the branch part 240 toward the inlet 222 side, for example, as illustrated in FIGS. 6 and 7. The holding space 230 communicates with the airflow passage 220 at the branch part 240. In addition, an end part of the holding space 230 on the inlet 222 side is separated from the outside by a sealing member 232 provided on the rear end face of the fragrance material holding member 200.

The holding space 230 is, for example, formed in the following manner: a penetration path is formed from the rear end face of the fragrance material holding member 200 to the branch part 240, and then an opening of the penetration path on the rear end face side of the fragrance material holding member 200 is sealed by the sealing member 232. Thus, the holding space 230 that communicates with the airflow passage 220 and is separated from the outside is formed. The sealing member 232 may be, for example, provided for each holding space 230 as illustrated in FIGS. 6 and 7. Note that the sealing member 232 is merely an example of a configuration for implementing a function of separating the holding space 230 from the outside. For example, the function may also be implemented by covering the rear end face of the fragrance material holding member 200 by a sheet having an opening at a position corresponding to a position of each inlet 222 of the airflow passage 220, and sealing, by the sheet, an opening of a penetration path formed in a formation process of the holding space 230.

Sending of air to the airflow passage 220 causes flow of air from the rear end side to the front end side of the airflow passage 220. A vaporized component of the fragrance material held by the airflow passage 220 is sent to the front end side of the airflow passage 220 by the flow of air caused in the airflow passage 220. In addition, the vaporized component of the fragrance material held by the holding space 230 flows out to the airflow passage 220 via the branch part 240 between the holding space 230 and the airflow passage 220 and is sent to the front end side of the airflow passage 220 by the flow of air caused in the airflow passage 220. Then, the vaporized component of the fragrance material sent to the front end side of the airflow passage 220 is discharged from the discharge port 110 of the lid 100.

Here, the plurality of pairs of the airflow passage 220 and the holding space 230 may be caused to hold different types of fragrance materials, in which case a fragrance provided by the fragrance providing device 1 can be switched by switching the airflow passage 220 that communicates with the flow channel 610 of the chassis 600. Note that the plurality of pairs of the airflow passage 220 and the holding space 230 may be caused to hold the same type of fragrance material. For example, duration of each fragrance material can be set appropriately in accordance with the frequency of use of each fragrance material by causing a larger number of pairs of the airflow passage 220 and the holding space 230 to hold a fragrance material used with higher frequency.

If the fragrance material holding member is not provided with the holding space 230 that branches from the airflow passage 220 and holds the fragrance material, the fragrance material may be held only by the airflow passage 220. On the other hand, in the fragrance providing device 1 according to the present embodiment, in addition to the airflow passage 220 in which flow of air for discharging a vaporized component of the fragrance material to the outside occurs, the holding space 230, which is a space different from the airflow passage 220, can also be caused to hold the fragrance material. This can increase the amount of the fragrance material that can be held by the entire fragrance material holding member 201. Therefore, providing the fragrance material holding member 201 with the holding space 230 can improve persistence of the fragrance material while avoiding an increase in the size of the device.

The fragrance material is, for example, held in a state of adhering to inner surfaces of the airflow passage 220 and the holding space 230. Therefore, as an inner surface area of the airflow passage 220 or the holding space 230 is larger, the amount of the fragrance material that can be held by the airflow passage 220 or the holding space 230 is larger. Hence, the amount of the fragrance material that can be held by the holding space 230 can be made larger than that of the airflow passage 220 by making the inner surface area of the holding space 230 larger than that of the airflow passage 220. In this case, the amount of the fragrance material that can be held by the entire fragrance material holding member 201 can be increased without causing the airflow passage 220 to hold the fragrance material.

The holding space 230 may have a curve shape. Thus, a path length of the holding space 230 can be made longer than that in the case where the holding space 230 is provided in a straight-line form. This can increase the amount of the fragrance material that can be held by the holding space 230, and thus can further improve the persistence of the fragrance material. FIG. 8 is a conceptual diagram for describing an example of a configuration of the fragrance material holding member 201 according to the first example. As illustrated in FIG. 8, in the first example, the holding space 230 is provided to branch from the branch part 240 of the airflow passage 220 provided in a straight-line form from the inlet 222 to the outlet 224.

Figure 8:
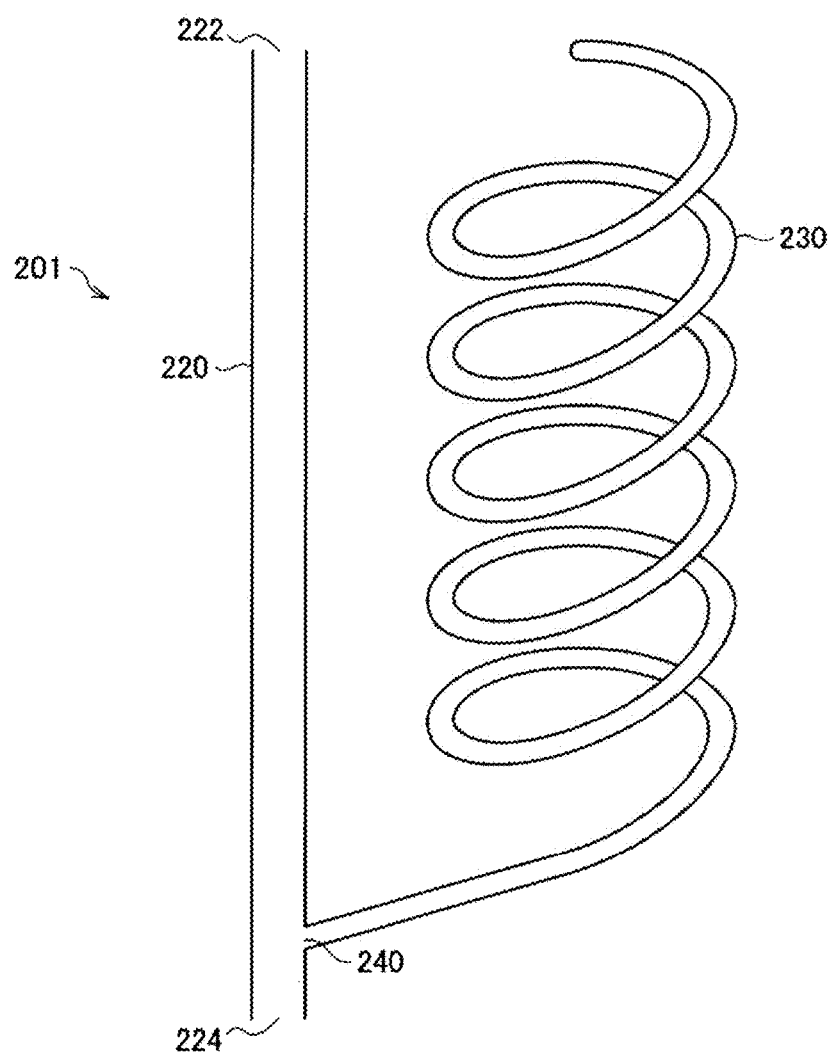
FIG. 8 is a conceptual diagram for describing an example of a configuration of the fragrance material holding member according to the first example.

Specifically, the holding space 230 according to the first example has a spiral shape as illustrated in FIG. 8. For example, the holding space 230 is provided to extend, in a spiral, from the branch part 240 toward the inlet 222 side along a direction in which the airflow passage 220 extends. In the first example, having the spiral shape, the holding space 230 does not have a bent portion where stress is likely to concentrate. Therefore, persistence of the fragrance material can be improved while strength of the fragrance material holding member 200 is improved.

In the first example, a twist axis of the spiral shape of the holding space 230 is located farther outside than an inner circumferential part of the fragrance material holding member 201 and farther inside than an outer circumferential part thereof, as illustrated in FIGS. 6 and 7. In addition, for example, the holding space 230 is located between the airflow passages 220 adjacent to each other. Providing the holding space 230 with the spiral shape in a manner that the twist axis is located farther outside than the inner circumferential part of the fragrance material holding member 201 and farther inside than the outer circumferential part thereof, as described above, can increase the amount of the fragrance material that can be held while effectively using a space between the airflow passages 220.

The locking groove 250 is provided on the outer circumferential part of the rear end side of the fragrance material holding member 201 to extend along the axial direction of the fragrance material holding member 201, as illustrated in FIGS. 6 and 7, to enable relative rotation of the chassis 600 and the fragrance material holding member 201 in the rotation mechanism 500. In the case where a holding member is used that holds the fragrance material holding member 201 and rotates integrally with the fragrance material holding member 201 in the relative rotation of the chassis 600 and the fragrance material holding member 201, the holding member is provided with a locking projection. In a state where the fragrance material holding member 201 is held by the holding member, the locking projection of the holding member is fitted to the locking groove 250 of the fragrance material holding member 201; thus, the fragrance material holding member 201 can be prevented from rotating with respect to the holding member.

2-2. Second Example

An example of the fragrance material holding member provided with a holding space with a spiral shape has been described, but an arrangement of the holding space in the fragrance material holding member is not limited to this example. A second example in which the arrangement of the holding space in the fragrance material holding member is different from that in the first example is described below with reference to FIGS. 9 and 10.

Figure 9:
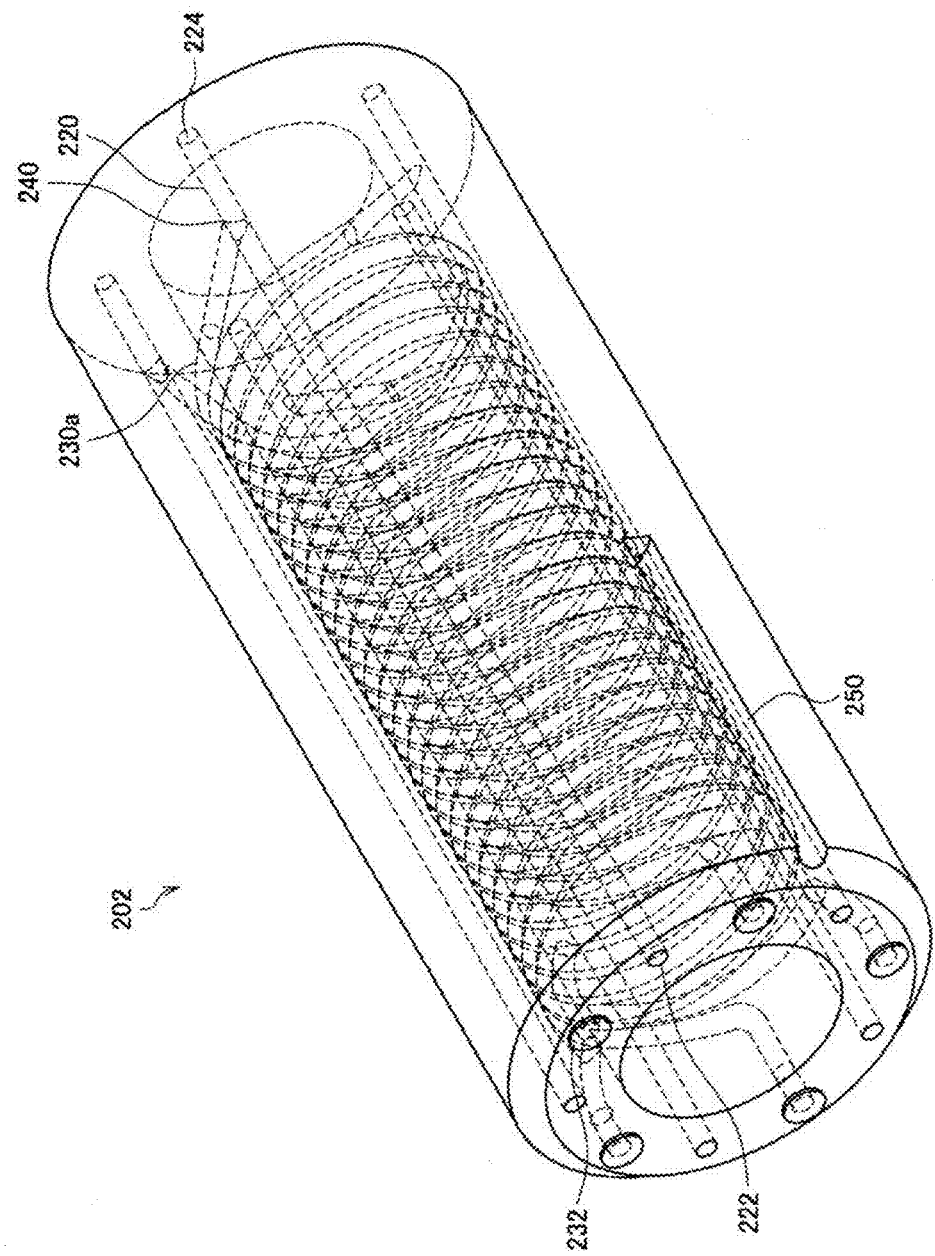
FIG. 9 is a perspective view of an example of a configuration of a fragrance material holding member according to a second example.
Figure 10:
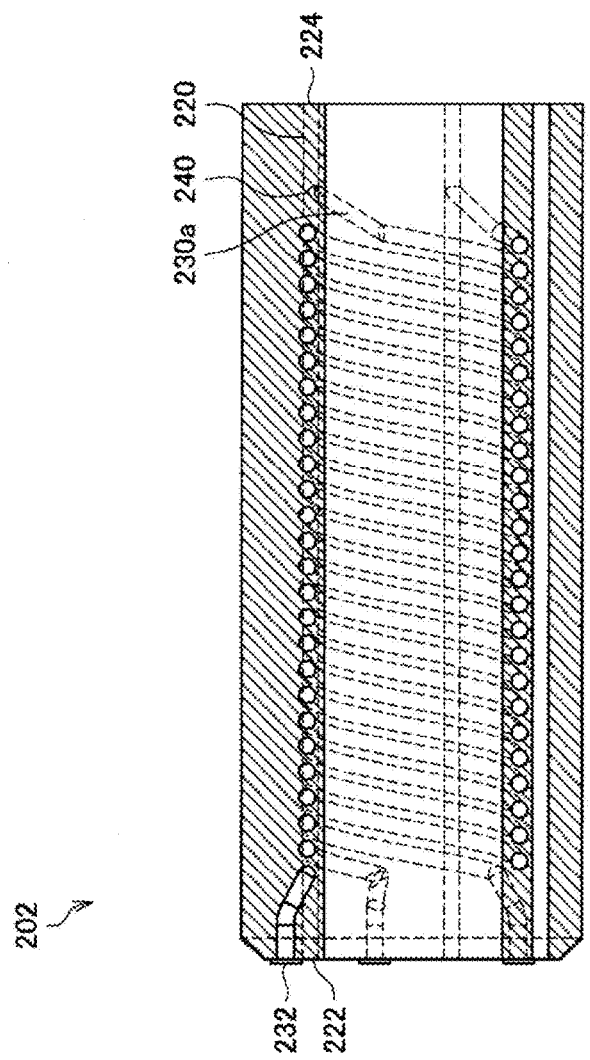
FIG. 10 shows a cross-sectional view and a side view of an example of a configuration of the fragrance material holding member according to the second example.
Figure 10:
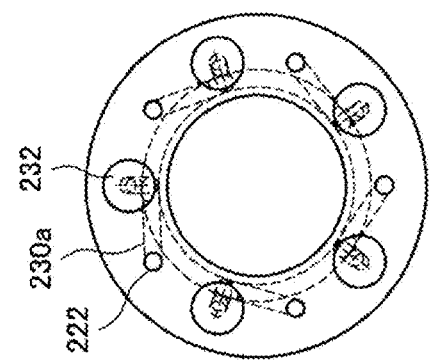

FIG. 9 is a perspective view of an example of a configuration of a fragrance material holding member 202 according to the second example. FIG. 10 shows a cross-sectional view and a side view of an example of a configuration of the fragrance material holding member 202 according to the second example. Specifically, FIG. 10 shows a cross-sectional view of the fragrance material holding member 202 along a cross-section passing through a central axis of the fragrance material holding member 202, and a side view of the fragrance material holding member 202 seen in the central axis direction. As illustrated in FIGS. 9 and 10, the fragrance material holding member 202 includes the airflow passage 220, a holding space 230a, and the locking groove 250. The holding space 230a according to the second example has a spiral shape and is provided to extend, in a spiral, from the branch part 240 toward the inlet 222 side along a direction in which the airflow passage 220 extends, as in the first example. On the other hand, in the second example, the position of a twist axis of the spiral shape of the holding space 230a in the fragrance material holding member 202 is different from that in the first example.

In the second example, the twist axis of the spiral shape of the holding space 230a is located farther inside than an inner circumferential part of the fragrance material holding member 202 as illustrated in FIGS. 9 and 10. Specifically, the twist axis of the spiral shape of the holding space 230a substantially coincides with the central axis of the fragrance material holding member 202. Therefore, the holding space 230a is provided to extend, in a spiral in a circumferential direction of the fragrance material holding member 202, along a direction in which the airflow passage 220 extends. For example, the holding spaces 230a that communicate with the respective airflow passages 220 may be configured to form a spiral in a state of being adjacent to each other. Providing the holding space 230a with the spiral shape in a manner that the twist axis is located farther inside than the inner circumferential part of the fragrance material holding member 202, as described above, can increase the amount of the fragrance material that can be held while effectively using a space near the inner circumferential part or the outer circumferential part of the fragrance material holding member 200 with a hollow tubular shape.

Figure 11:
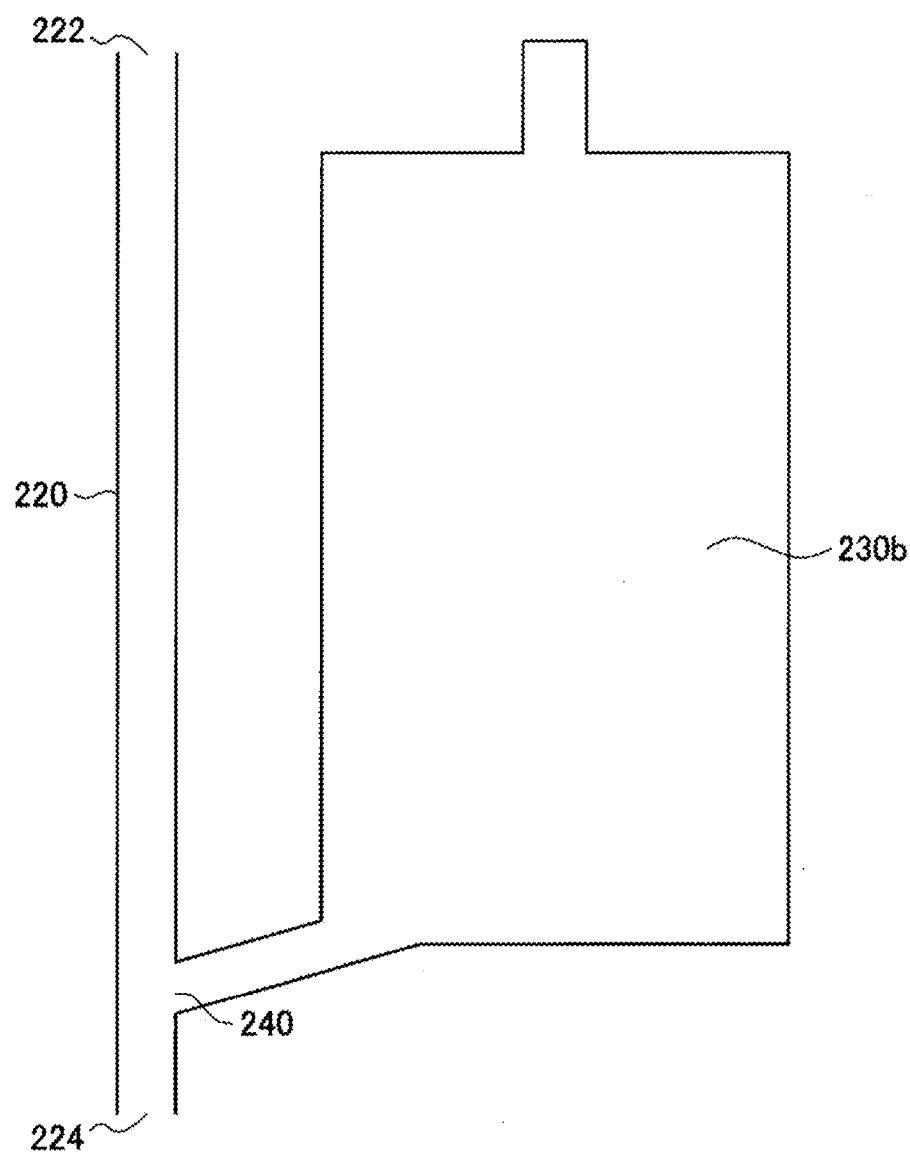
FIG. 11 is a conceptual diagram for describing an example of a configuration of a fragrance material holding member according to another embodiment.

An example in which the holding space has a curve shape has been described, but the shape of the holding space is not limited to this example. For example, the holding space may be provided in a straight-line form. FIG. 11 is a conceptual diagram for describing an example of a configuration of a fragrance material holding member according to another embodiment. In the example illustrated in FIG. 11, a holding space 230b is provided in a straight-line form to branch from the branch part 240 of the airflow passage 220 provided in a straight-line form from the inlet 222 to the outlet 224. In addition, the holding space 230b in this example has its diameter expanded on the inlet 222 side with respect to the branch part 240, as illustrated in FIG. 11. Thus, an inner surface area of the holding space 230b can be made larger than that in the case where the holding space 230b has a shape whose diameter is not expanded after branching at the branch part 240. This can increase the amount of the fragrance material that can be held by the holding space 230b, and thus can further improve the persistence of the fragrance material.

2-3. Effect

Figure 12:
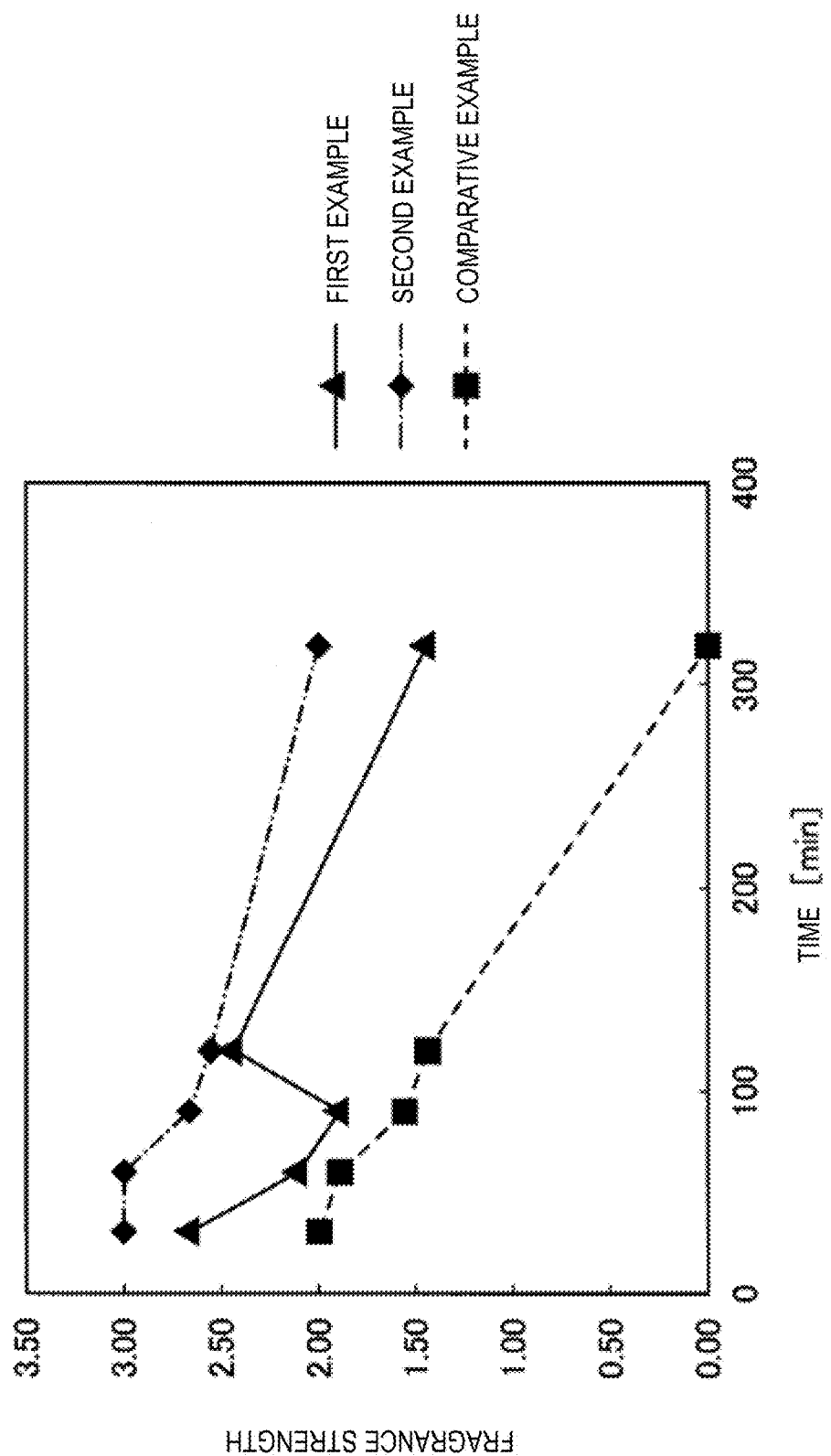
FIG. 12 is an explanatory diagram for describing persistence of a fragrance material in the present embodiment.

Now, an effect of improving persistence of a fragrance material of the present embodiment will be described. FIG. 12 is an explanatory diagram for describing persistence of a fragrance material in the present embodiment. A comparative example in FIG. 12 indicates an example in which a fragrance material holding member is used that does not include a holding space branching from an airflow passage and holds a fragrance material only in the airflow passage, unlike in the first example and the second example described above. FIG. 12 shows, in regard to the first example, the second example, and the comparative example, test results of the strength of a fragrance provided to the outside of the device by the fragrance providing device at each time after start of use of the fragrance material holding member. As shown in FIG. 12, the strength of the fragrance provided to the outside of the device at each time in the first example and the second example is higher than that in the comparative example. In other words, an amount of decrease of fragrance strength per unit time in the first example and the second example is smaller than that in the comparative example. The results demonstrate that persistence of a fragrance material can be improved according to the present embodiment.

3. Modification Examples

Now, various modification examples according to the present disclosure will be described.

3-1. First Modification Example

First, a first modification example that can further improve straightness of air that includes a vaporized component of the fragrance material and is discharged to the outside of the device is described with reference to FIG. 13.

Figure 13:
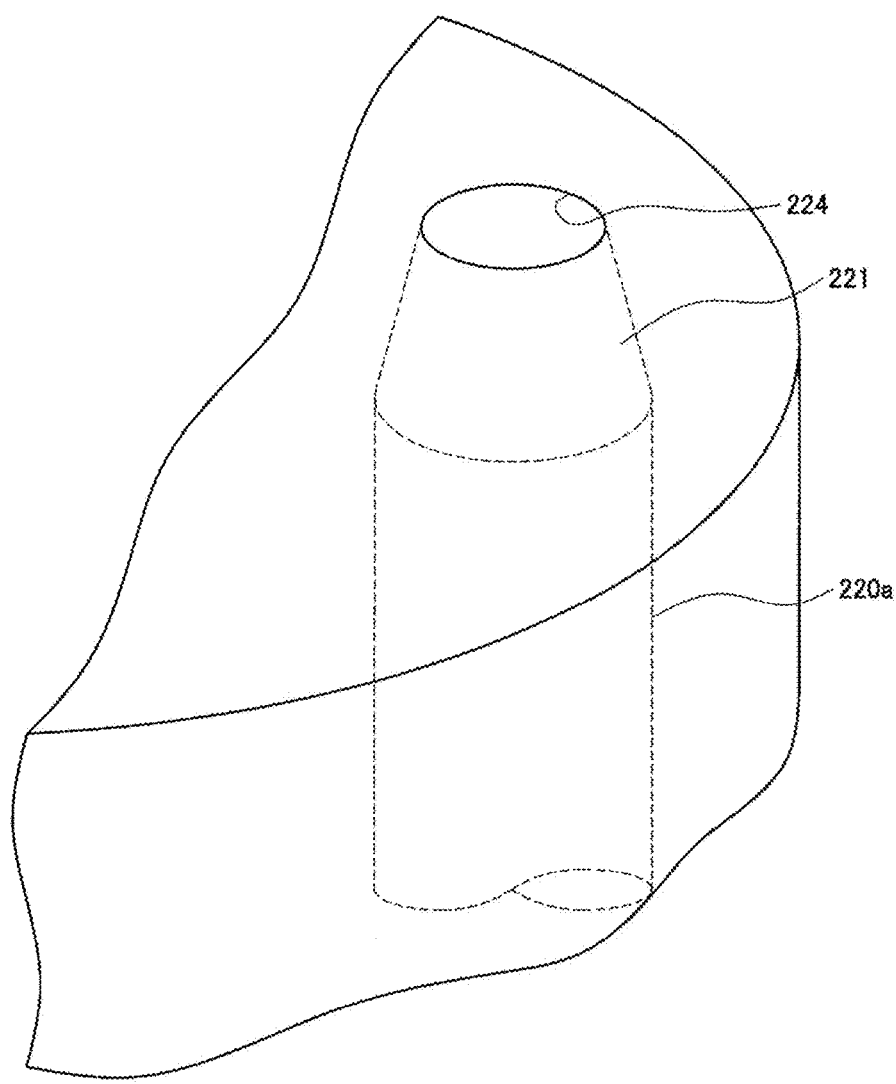
FIG. 13 is an explanatory diagram illustrating an example of a configuration of an airflow passage according to a first modification example.

FIG. 13 is an explanatory diagram illustrating an example of a configuration of an airflow passage 220a according to the first modification example. As illustrated in FIG. 13, a tapered part 221 whose diameter is reduced toward the outlet 224 is provided on the outlet 224 side of the airflow passage 220a according to the first modification example. Thus, air sent from the airflow passage 220a to the outlet 224 can be narrowed. This can suppress diffusion of air released from the outlet 224, and thus can further improve straightness of air that includes a vaporized component of the fragrance material and is discharged to the outside of the device. Note that a position at which diameter reduction of the airflow passage 220a is started by the tapered part 221 and a taper angle of the tapered part 221 may be set as appropriate in accordance with dimensions of the airflow passage 220a, pressure of air supplied to the airflow passage 220a, and the like. In addition, a similar effect can be obtained also by providing the discharge port 110 of the lid 100 that communicates with the outlet 224 with a tapered part whose diameter is reduced toward the front end side.

3-2. Second Modification Example

Figure 14:
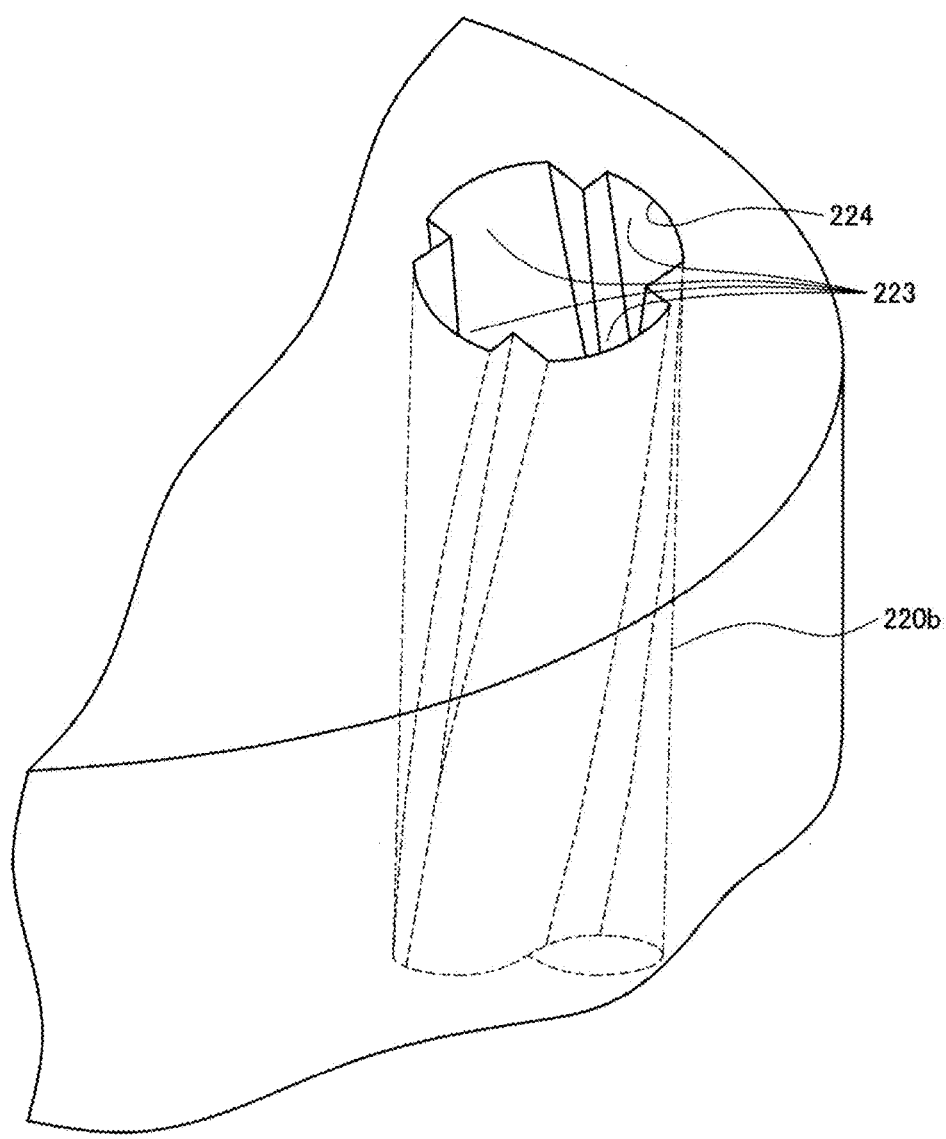
FIG. 14 is an explanatory diagram illustrating an example of a configuration of an airflow passage according to a second modification example.

Now, a second modification example having another configuration for obtaining an effect similar to that in the first modification example will be described with reference to FIG. 14. FIG. 14 is an explanatory diagram illustrating an example of a configuration of an airflow passage 220b according to the second modification example. As illustrated in FIG. 14, the surface inside the airflow passage 220b according to the second modification example is provided with grooves 223 with a spiral shape. Thus, slewing motion can be imparted to air released from the outlet 224, and straightness can be improved by a gyro effect. This can further improve straightness of air that includes a vaporized component of the fragrance material and is discharged to the outside of the device. Note that the number of the grooves 223 or the shape of a transverse section thereof is not limited to the example illustrated in FIG. 14, and may be another number or another shape of a transverse section.

3-3. Third Modification Example

Figure 15:
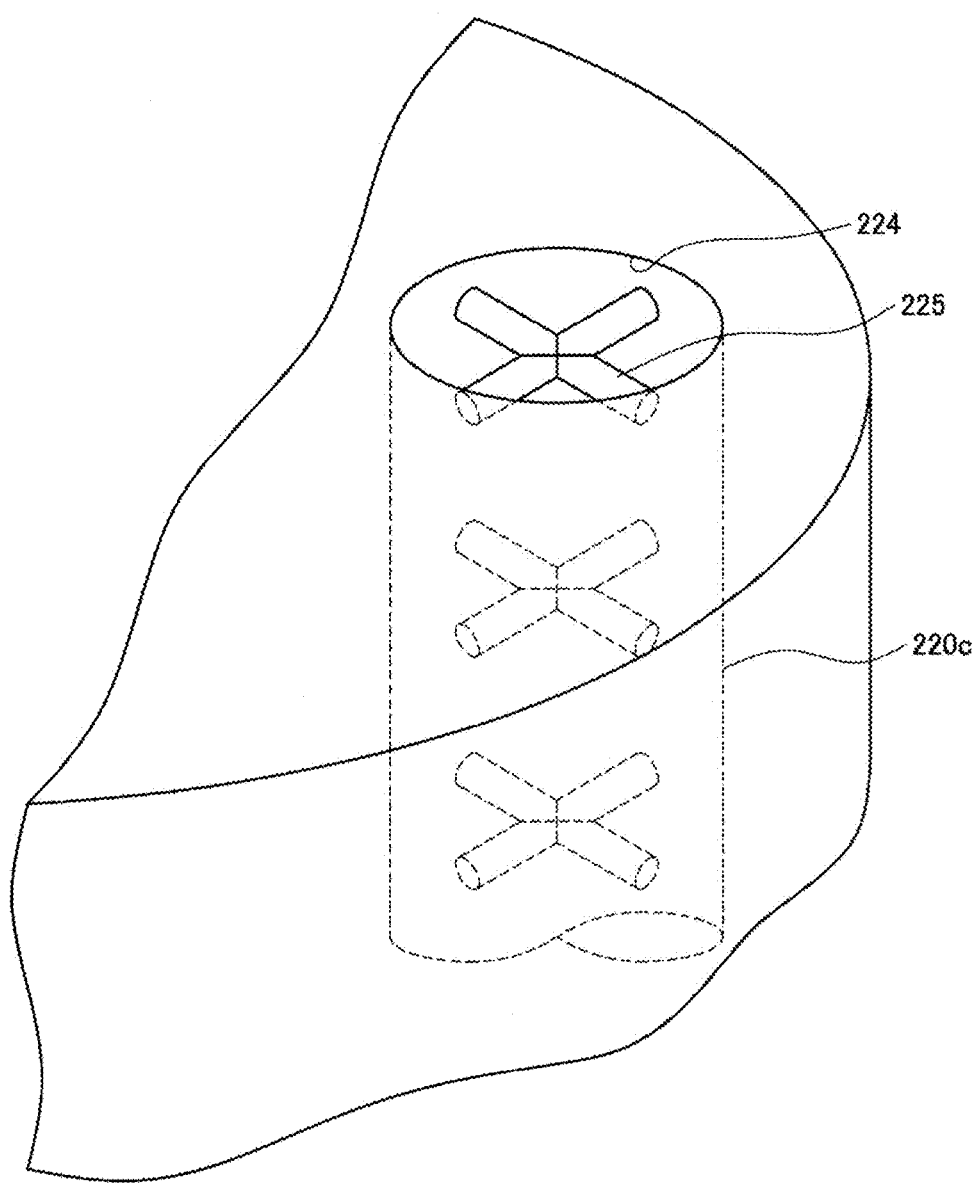
FIG. 15 is an explanatory diagram illustrating an example of a configuration of an airflow passage according to a third modification example.

Next, a third modification example that can increase the amount of the fragrance material that can be held by the fragrance material holding member 200 is described with reference to FIG. 15. FIG. 15 is an explanatory diagram illustrating an example of a configuration of an airflow passage 220c according to the third modification example. As illustrated in FIG. 15, a surface increasing part 225 that increases the surface inside the airflow passage 220c is provided in the airflow passage 220c according to the third modification example. The surface increasing part 225 may have, for example, a shape with rotational symmetry around a central axis of the airflow passage 220c. Specifically, the surface increasing part 225 may include two cylinders that intersect the central axis of the airflow passage 220c and are orthogonal to each other, as illustrated in FIG. 15. Thus, the fragrance material is caused to be held in a state of adhering to the surface of the surface increasing part 225, which can increase the amount of the fragrance material that can be held by the fragrance material holding member 200. Note that the shape and structure of the surface increasing part 225 are not particularly limited as long as the surface increasing part 225 has a function of increasing the surface inside the airflow passage 220c, and for example, the surface increasing part 225 may be a protrusion projecting from an inner surface of the airflow passage 220c toward the inside of the airflow passage 220c. In addition, the position of the surface increasing part 225 in the airflow passage 220c may be set as appropriate.

3-4. Fourth Modification Example

Figure 16:
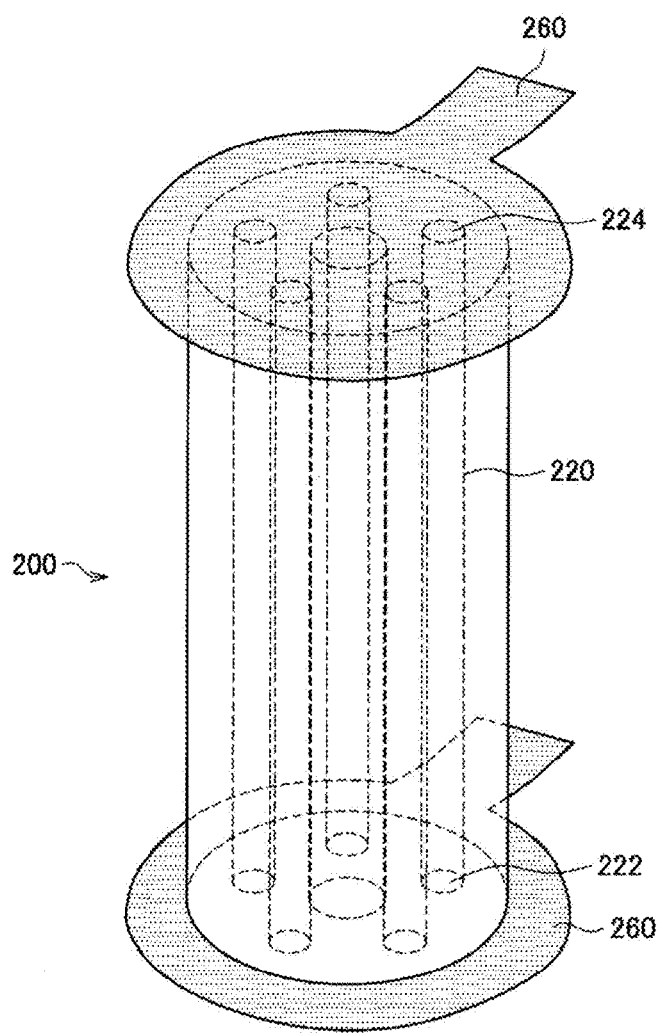
FIG. 16 is an explanatory diagram illustrating an example of a configuration of a sealing member according to a fourth modification example.
Figure 17:
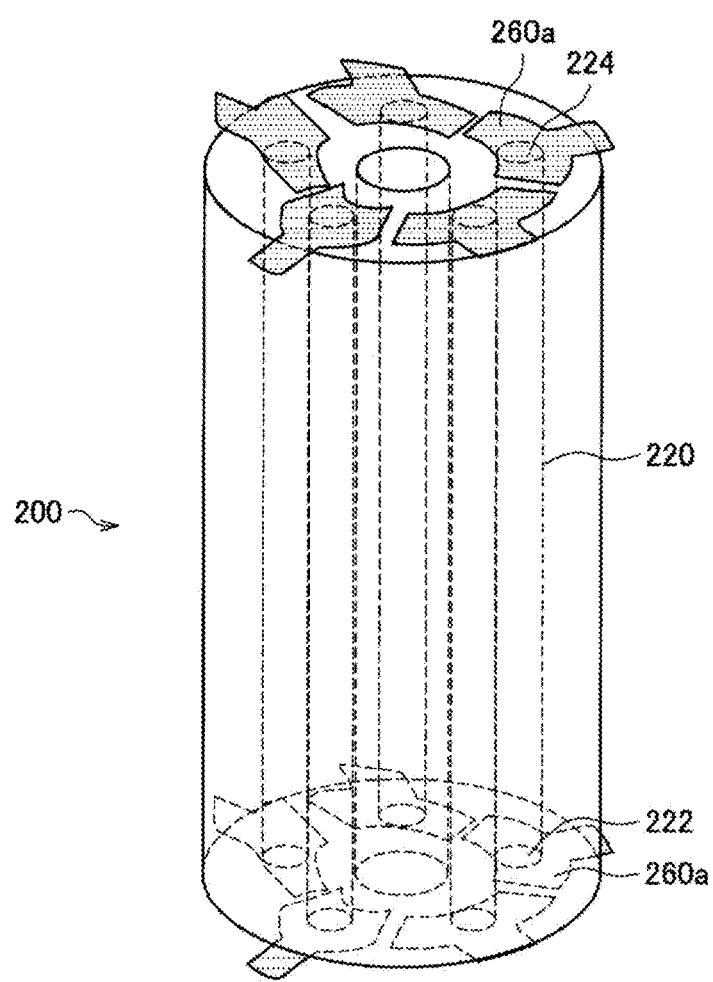
FIG. 17 is an explanatory diagram illustrating an example of a configuration of a sealing member according to another embodiment.

Next, a fourth modification example that can suppress oxidation of a fragrance material due to entry of air into the fragrance material holding member 200 when the fragrance material holding member 200 is not used, such as during storage or during transportation, is described with reference to FIGS. 16 and 17. FIG. 16 is an explanatory diagram illustrating an example of a configuration of a sealing member 260 according to the fourth modification example. In the fourth modification example, the inlet 222 and the outlet 224 of the airflow passage 220 of the fragrance material holding member 200 are sealed by the sealing member 260. The sealing member 260 is removed from the fragrance material holding member 200 when the fragrance material holding member 200 is used. In this manner, entry of air from the outside into the fragrance material holding member 200 can be suppressed when the fragrance material holding member 200 is not used. This can suppress oxidation of the fragrance material.

The sealing member 260 may be, for example, a heat seal film. In addition, the sealing member 260 may be able to seal all or part of a plurality of inlets 222 or outlets 224. For example, as illustrated in FIG. 17, a sealing member 260a capable of sealing one inlet 222 or outlet 224 may be provided for each inlet 222 or outlet 224. Thus, when the fragrance material holding member 200 is used, the sealing member 260a corresponding to a fragrance material selected by the user can be preferentially removed from the fragrance material holding member 200, and the fragrance providing device can be used without removing the sealing member 260a corresponding to another fragrance material.

3-5. Fifth Modification Example

Figure 18:
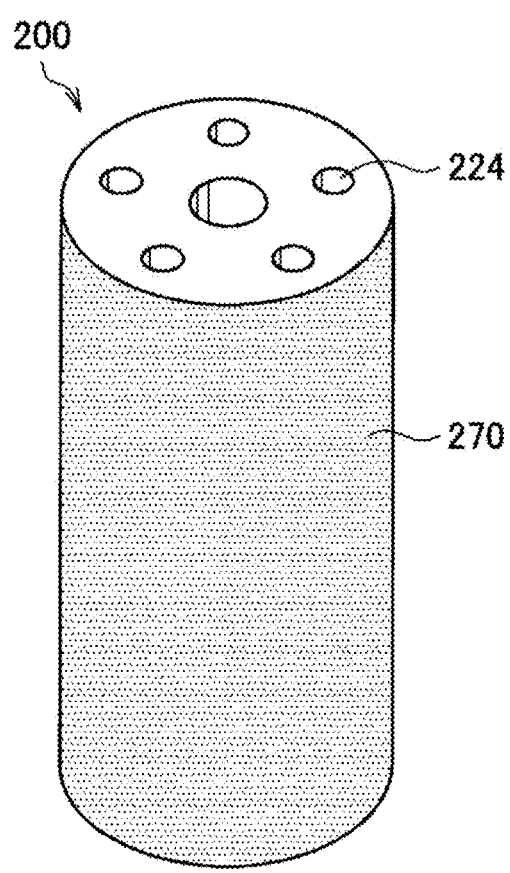
FIG. 18 is an explanatory diagram illustrating an example of a configuration of a light-blocking member according to a fifth modification example.

Now, a fifth modification example that can suppress oxidation of a fragrance material due to irradiation of the fragrance material with light when the fragrance material holding member 200 is not used, such as during storage or during transportation, will be described with reference to FIG. 18. FIG. 18 is an explanatory diagram illustrating an example of a configuration of a light-blocking member 270 according to the fifth modification example. In the fifth modification example, part or the whole of the fragrance material holding member 200 is covered by the light-blocking member 270, which is a member that blocks light. For example, as illustrated in FIG. 18, the light-blocking member 270 is provided to cover the outer circumferential surface of the fragrance material holding member 200 when the fragrance material holding member 200 is not used. In this manner, irradiation of the fragrance material held in the fragrance material holding member 200 with light, such as sunlight or light emitted by lighting equipment, can be suppressed when the fragrance material holding member 200 is not used. This can suppress oxidation of the fragrance material.

4. Conclusion

As described above, according to an embodiment of the present disclosure, the airflow passage 220 through which air supplied from the air pump 300 passes is provided to penetrate. The holding space 230 branches from the airflow passage 220 and holds the fragrance material. Thus, in addition to the airflow passage 220 in which flow of air for discharging a vaporized component of the fragrance material to the outside occurs, the holding space 230, which is a space different from the airflow passage 220, can also be caused to hold the fragrance material. This can increase the amount of the fragrance material that can be held by the entire fragrance material holding member 201. Therefore, providing the fragrance material holding member 201 with the holding space 230 can improve persistence of the fragrance material while avoiding an increase in the size of the device.

Described above is an example in which one airflow passage 220 among the plurality of airflow passages 220 communicates with the flow channel 610 of the chassis 600 that introduces the air supplied from the air pump 300 to the airflow passage 220; however, the technical scope of the present disclosure is not limited to this example. For example, the flow channel 610 may communicate with two or more airflow passages 220 at the same time.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A fragrance material holding member including:

an airflow passage through which air supplied from an airflow source passes, the airflow passage being provided to penetrate the fragrance material holding member; and a holding space that branches from the airflow passage and holds a fragrance material.

(2)

The fragrance material holding member according to (1), in which the holding space has a curve shape.

(3)

The fragrance material holding member according to (2), in which the curve shape is a spiral shape.

(4)

The fragrance material holding member according to (3), in which the fragrance material holding member has a hollow tubular shape, and a twist axis of the spiral shape is located farther outside than an inner circumferential part of the fragrance material holding member and farther inside than an outer circumferential part of the fragrance material holding member.

(5)

The fragrance material holding member according to (3), in which the fragrance material holding member has a hollow tubular shape, and a twist axis of the spiral shape is located farther inside than an inner circumferential part of the fragrance material holding member.

(6)

The fragrance material holding member according to any one of (1) to (5), in which a tapered part whose diameter is reduced toward an outlet is provided on the outlet side of the airflow passage from which the air is released.

(7)

The fragrance material holding member according to any one of (1) to (6), in which a groove with a spiral shape is provided on a surface inside the airflow passage.

(8)

The fragrance material holding member according to any one of (1) to (7), in which a surface increasing part that increases a surface inside the airflow passage is provided in the airflow passage.

(9)

A fragrance providing device including:

a fragrance material holding member including an airflow passage through which air supplied from an airflow source passes, the airflow passage being provided to penetrate the fragrance material holding member, and a holding space that branches from the airflow passage and holds a fragrance material; and the airflow source that supplies the air to the airflow passage.

REFERENCE SIGNS LIST 1, 1a providing device
100 lid
110 discharge port
200, 201, 202 fragrance material holding member
220, 220a, 220b, 220c airflow passage
221 tapered part
222 inlet
223 groove
224 outlet
225 surface increasing part
230, 230a, 230b holding space 232 sealing member
240 branch part
250 locking groove
260, 260a sealing member
270 light-blocking member
300 air pump
310 motor
400 battery
500 rotation mechanism
600 chassis
610 flow channel
700, 710 switch
800 substrate

The invention claimed is:

1. A fragrance material holding member comprising:
an airflow passage through which air supplied from an airflow source passes, the airflow passage extending along a first axis;
a branch part that branches at least initially along a second axis directly from the airflow passage, wherein the branch part has a smaller diameter than the airflow passage, and wherein the second axis is not parallel to the first axis; and
a holding space holding a fragrance material,
wherein the holding space is in fluid communication with the airflow passage at the branch part,
wherein the holding space has a curve shape,
wherein the curve shape is a spiral shape,
wherein the fragrance material holding member has a hollow tubular shape, and
wherein a twist axis of the spiral shape is located farther outside than an inner circumferential part of the fragrance material holding member and farther inside than an outer circumferential part of the fragrance material holding member.

2. The fragrance material holding member according to claim 1, wherein a tapered part whose diameter is reduced toward an outlet is provided on an outlet side of the airflow passage from which the air is released.

3. The fragrance material holding member according to claim 1, wherein a groove with a spiral shape is provided on a surface inside the airflow passage.

4. The fragrance material holding member according to claim 1, wherein a surface increasing part that increases a surface inside the airflow passage is provided in the airflow passage.

5. The fragrance material holding member according to claim 1, wherein the fragrance material is an essential oil or an essential oil diluted in ethanol.

6. A fragrance providing device comprising:
a fragrance material holding member including
an airflow passage through which air supplied from an airflow source passes, the airflow passage extending along a first axis;
a branch part that branches at least initially along a second axis directly from the airflow passage, wherein the branch part has a smaller diameter than the airflow passage, and wherein the second axis is not parallel to the first axis;
the airflow source that supplies the air to the airflow passage; and
a holding space holding a fragrance material,
wherein the holding space is in fluid communication with the airflow passage at the branch part, and
wherein:
the fragrance material holding member includes:
a plurality of airflow passages including the airflow passage, and
a plurality of holding spaces including the holding space, and
the fragrance providing device further comprises a rotation mechanism for rotating the member for switching the airflow passage to which the air is supplied, wherein a driving circuit drives the rotation mechanism.

7. The fragrance providing device according to claim 6, wherein the fragrance material is an essential oil or an essential oil diluted in ethanol.

8. The fragrance providing device according to claim 6, wherein the driving circuit performs control for switching between the plurality of airflow passages to which the air is supplied based on an input signal.

9. The fragrance providing device according to claim 6, wherein the airflow source is controlled by an input signal for supply of air.

10. The fragrance providing device according to claim 8, wherein the input signal is generated based on an operation on a switch by a user.

11. The fragrance providing device according to claim 9, wherein the input signal is generated based on an operation on a switch by a user.

* * * * *